US006102882A

United States Patent [19]

Cobo

[11] Patent Number: 6,102,882

[45] Date of Patent: Aug. 15, 2000

[54] PHYSIOTHERAPY APPARATUS FOR THE TREATMENT OF ARTICULAR STIFFNESS

[76] Inventor: Bernabe Cobo Cobo, Calle Gavina, 28, E-08290 Cerdanyola del Vallés, Spain

[21] Appl. No.: 08/973,673

[22] PCT Filed: Apr. 15, 1996

[86] PCT No.: PCT/ES97/00087

§ 371 Date: Dec. 10, 1997

§ 102(e) Date: Dec. 10, 1997

[87] PCT Pub. No.: WO97/38660

PCT Pub. Date: Oct. 23, 1997

[30] Foreign Application Priority Data

Apr. 15, 1996 [ES] Spain .................................... 9600902

[51] Int. Cl.[7] ...................................................... A61M 1/00

[52] U.S. Cl. ............................ 602/32; 606/243; 606/242

[58] Field of Search .................................... 606/237, 238, 606/239, 240, 241, 242, 243, 244, 84–87, 245; 602/32, 33, 35, 36, 38, 39; 5/610, 611, 607, 608, 612; 601/49, 86, 90, 98

[56] References Cited

U.S. PATENT DOCUMENTS

| | | | |
|---|---|---|---|
| 1,280,987 | 10/1918 | Gregory | 606/241 |
| 1,282,580 | 10/1918 | Hosford et al. | 606/241 |
| 1,427,004 | 8/1922 | McManis | 606/244 |
| 1,950,948 | 3/1934 | Murray | 606/242 |
| 2,377,940 | 6/1945 | Hughes | 602/39 |
| 2,798,481 | 7/1957 | Matthews | 606/241 |
| 2,950,715 | 8/1960 | Brobeck | 606/243 |
| 3,420,229 | 1/1969 | Miller | 606/243 |
| 3,565,217 | 2/1971 | Louis | 187/27 |
| 3,598,405 | 8/1971 | Burns | 482/145 |
| 3,620,210 | 11/1971 | Annas . | |
| 3,771,518 | 11/1973 | Greissing | 606/243 |
| 4,144,880 | 3/1979 | Daniels | 606/242 |
| 4,257,410 | 3/1981 | Flewelling | 602/33 |
| 4,356,816 | 11/1982 | Granberg | 606/243 |
| 4,432,356 | 2/1984 | Sarrell et al. | 602/32 |
| 4,539,978 | 9/1985 | Lundblad | 606/243 |
| 4,579,109 | 4/1986 | Lundbladq | 606/243 |
| 4,602,619 | 7/1986 | Wolf et al. | 606/241 |
| 4,700,696 | 10/1987 | Schoffstall | 606/242 |
| 4,850,343 | 7/1989 | Scott | 606/238 |
| 5,094,228 | 3/1992 | Reinert | 606/243 |
| 5,099,828 | 3/1992 | Duke . | |
| 5,147,287 | 9/1992 | Jewell et al. | 602/33 |
| 5,179,745 | 1/1993 | Hebert et al. | 5/620 |
| 5,192,306 | 3/1993 | Scott et al. | 606/243 |
| 5,217,487 | 6/1993 | Engel et al. | 606/240 |
| 5,300,090 | 4/1994 | Primic | 606/243 |
| 5,308,359 | 5/1994 | Lossing | 606/242 |
| 5,320,640 | 6/1994 | Riddle et al. | 606/243 |
| 5,401,236 | 3/1995 | Summerville | 606/241 |
| 5,409,452 | 4/1995 | Aversano | 606/241 |
| 5,417,634 | 5/1995 | Habing | 482/99 |
| 5,423,861 | 6/1995 | Kelley | 606/241 |
| 5,444,882 | 8/1995 | Andrews et al. | 5/618 |
| 5,575,765 | 11/1996 | Foster | 602/32 |
| 5,645,079 | 7/1997 | Zahiri et al. | 5/610 |
| 5,865,782 | 2/1999 | Tuite | 602/32 |

FOREIGN PATENT DOCUMENTS

| | | | |
|---|---|---|---|
| 1226506 | 7/1960 | France | 600/243 |
| 273787 | 7/1983 | Spain . | |
| 8402075 | 6/1984 | WIPO . | |
| 8803791 | 6/1988 | WIPO . | |

*Primary Examiner*—Richard J. Apley
*Assistant Examiner*—Justine R. Yu
*Attorney, Agent, or Firm*—Steinberg & Raskin, P.C.

[57] ABSTRACT

Physiotherapy apparatus for the treatment of articular stiffness including a table for a patient having a static board, a moving board which is displaceable towards and away from the static board and a device for applying a traction force between parts of the patient's body. The moving board is mounted such that it can also rotate about a horizontal axis between a horizontal position and an inclined position, and about a vertical axis between two extreme positions which are symmetrical with respect to a longitudinal axis of the table. The device for applying a traction force includes a traction cord and a system of pulleys with which the cord is associated in order to apply the traction to a joint of the patient in a desired direction. The apparatus is highly versatile, permitting treatment of cervical and lumbar vertebrae, hip, shoulder, elbow, wrist, knee and ankle.

22 Claims, 10 Drawing Sheets

PHYSIOTHERAPY APPARATUS FOR THE TREATMENT OF ARTICULAR STIFFNESS

The present invention relates to a physiotherapy apparatus of the type used for the treatment of articular rigidity by means of passive mobilizations, through the application of controlled mechanical traction forces.

BACKGROUND OF THE INVENTION

Some known physiotherapy apparatuses present a table, similar to a stretcher, which has a displaceable part, for example for applying traction axially to the cervical and lumbar column of a patient.

There also exist specific apparatuses for the treatment of certain joints, such as the knee.

The known apparatuses nevertheless have the disadvantage of being rather unversatile, for they can be used only for some specific applications. This makes it difficult to amortize their cost, especially in the case of relatively small treatment facilities, which have to have a whole range of apparatuses of this type. Moreover, not all the mobilization movements are covered by the known apparatuses, and many of said movements have to be carried out manually. Another disadvantage associated with known apparatuses is the absence of reliable systems for controlling the force and the traction cycles which are applied to the patient, while also permitting adaptation to each specific case.

The above-mentioned apparatuses also have the disadvantage that it is not always possible to secure the parts of the patient's body in an optimum manner, and it can therefore occur that, for example, the traction is not limited to the joint to be treated.

DESCRIPTION OF THE INVENTION

The objective of the present invention is to resolve the aforesaid disadvantages, by means of a physiotherapy apparatus which is highly versatile and permits treatment of the cervical and lumbar vertebrae, hip, shoulder, elbow, knee and ankle, simply by displacing the position of some members of the apparatus, and which at the same time permits reliable, adjusted control of the traction cycles and can adapt them to the specific needs of each patient.

In accordance with these objectives, the physiotherapy apparatus of the invention for the treatment of articular rigidity comprises a table on which the patient is placed, made up of a static board and a moving board, with said moving board being displaceable towards and away from the static board, and means for applying a traction force between parts of the patient's body; and it is characterized in that the said moving board is mounted in such a way that it can also rotate about a horizontal axis, between a horizontal position and an inclined position, and about a vertical axis, between two end positions which are symmetrical with respect to the longitudinal axis of the table, and in that the said means for applying a traction force between parts of the patient's body include at least one traction cord and a system of pulleys with which said cord is associated in order to apply the traction to a joint of the patient in a desired direction.

According to one characteristic of the invention, the moving board comprises: a lower base attached to a horizontal bar, which can rotate with respect to some supporting uprights of the table, such that the board rotates between said horizontal and inclined positions; an upper plate, which can rotate with respect to said lower base about an axis perpendicular thereto, in order to effect rotation between said two symmetrical end positions; and a pair of guides, fixed to said upper plate, upon which the moving board can be displaced towards and away from the board.

Preferably, the apparatus is provided with elastic means which tend to keep the moving part in a symmetrical position with respect to the longitudinal axis of the table and close to the fixed board.

In accordance with another aspect of the invention, the static board is made up of a first end member articulated around a first horizontal axis, a fixed second end member, a first intermediate member articulated around a second horizontal axis parallel to the first axis and a second intermediate member articulated around a third horizontal axis parallel to the first and second axes.

Advantageously, the height of the table can also be adjusted.

In one embodiment, the moving board can rotate around the vertical axis through an angle of up to about 30° in each direction from an initial position of symmetry, and can rotate around the horizontal axis through an angle of up to about 50°.

In one embodiment, the apparatus also includes a plurality of anchorage points for releasable attachment of straps for securing the various parts of the patient to the static board and to the moving board.

Preferably, these anchorage points are formed by horizontal rods fixed to the upper surfaces of the boards, the boards being fitted with covers of flexible material which have openings in correspondance with said rods, and whose thickness is sufficient so that the anchoring rods do not project from them.

In a preferred embodiment of the invention, the apparatus comprises a base, on which are mounted the supporting uprights of the table and a supporting structure for an adjustable traction motor to which are attached two traction cords, the aforesaid system of pulleys comprising at least one driving pulley situated on the support structure beside the motor, one double return-pulley situated at the end of the base adjacent to the motor-support structure, a pair of horizontal pulleys situated at the opposite end of the base with respect to said return-pulley, each one of which guides one of the two traction cords through an arc of 180°, and a pair of pulleys displaceable along corresponding longitudinal guides fixed to the base of the apparatus, each one of said displaceable pulleys guiding one of the two cords to orient it in a desired direction.

According to a variant of this embodiment, the pulley system also includes a pair of pulleys which can move vertically along two guides fixed to the motor support structure, and a pair of pulleys which can move horizontally along a guide mounted on the motor support structure, this latter guide being able to move vertically.

In another variant, the pulley system also includes at least one pulley mounted on a support for cervical vertebrae traction, which can be fixed releasably on the motor support structure.

Advantageously, the physiotherapy apparatus further includes a set of two parallel guides which is mounted laterally with respect to the table and at an adjustable distance therefrom, at least one lateral pulley mounted on a slider being able to slide along said guides.

Also advantageously, the apparatus includes another guide on which a central pulley can move, said guide being mounted attached to the lower base of the moving board, substantially perpendicular thereto and centered on the longitudinal axis of the table.

Preferably, at least one of the aforesaid pulleys has associated to it a cord-direction guiding pulley mounted perpendicularly to it and having a rotation axis mounted in such a way that it can turn around it.

According to a preferential characteristic of the invention the apparatus also includes supports for the legs, mounted adjustably and releasably on the moving board, and attachments for the feet, with adjustable inclination and position, mounted releasably on the base of the apparatus.

Preferably onto one of the end members of the static board are fixed laterally a pair of vertical, telescopic bars, bearing at their upper ends rods for the attachment of straps for securing the shoulderblades of a patient.

The apparatus includes straps for securing the patient or for coupling with the traction cords, which straps, in one embodiment, have a band destined to extend around one part of the patient's body, to which are linked two tubular fitments provided with means of adjustment for the two cords which are inserted into same.

In an alternative embodiment, the straps have a band destined to extend around one part of the patient's body, to which band is attached a strip whose free end forms an eye for coupling with the aforesaid anchoring rods provided on the surfaces of the boards.

Advantageously, a control module is associated with the adjustable traction motor, the module having a plurality of pushbuttons for setting the treatment parameters, a starting pushbutton, displays for the selected parameters, indicator lights for the selected treatment and treatment phases, a set of alarms, an emergency stop button and a connector for a remote-control cable.

The motor control module can be used to program, display and monitor various parameters of the treatments, such as traction force, relaxation force, traction time, time of the traction/relaxation cycle, total treatment time, traction and relaxation speeds and others.

Preferably, the control module includes a non-volatile memory for storing the standard values for each treatment.

A standard program can thus be executed for each case, or one, several or all of the treatment parameters can be changed, thereby effecting a re-adjustment which makes all the values of force, time of each phase, traction speed, etc., suitable for the severity of the pathology and physical constitution of the patient, without deprogramming the session started.

Advantageously, the motor support structure is fitted with a pair of horizontal telescopic bars provided on one of their ends with at least two pulleys. These horizontal bars permit the cervical-vertebra traction forces to be oriented to any desired degree.

Preferably, the physiotherapy apparatus of the invention can also include a guide, which is mounted laterally with respect to the table and at an adjustable distance from same, on which guide can slide a vertical telescopic bar provided with at least two pulleys on at least one of its ends.

Advantageously, the physiotherapy apparatus of the invention can be taken apart into at least three parts to facilitate transportation thereof.

BRIEF DESCRIPTION OF THE DRAWINGS

For a better understanding of all that has been set out some drawings are attached which show, schematically and solely by way of non-restrictive example, a practical case of embodiment of the apparatus.

In said drawings.

DESCRIPTION OF A PREFERRED EMBODIMENT

Figure 1:
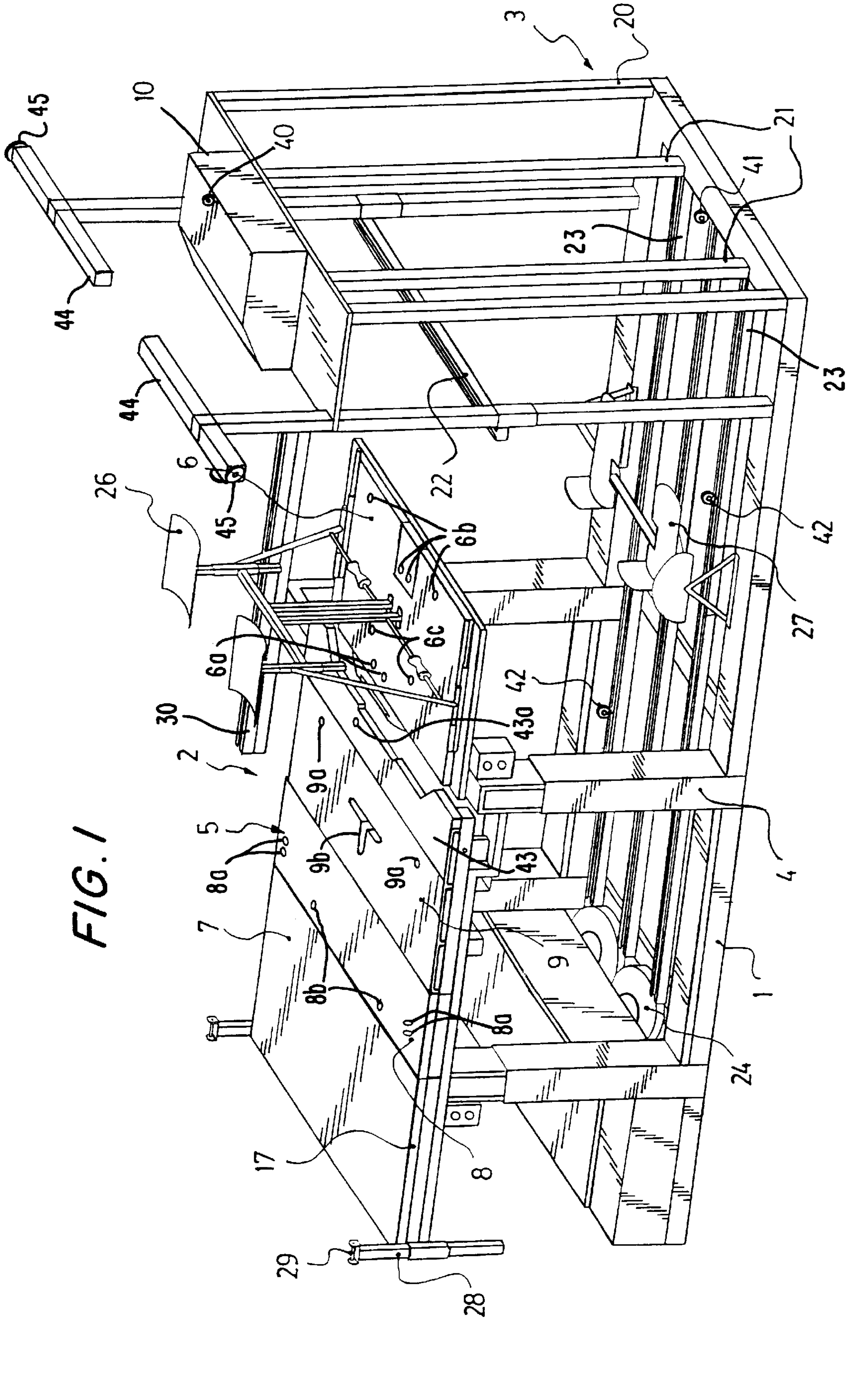
FIG. 1 is a perspective view of the physiotherapy apparatus of the invention.

One embodiment of the physiotherapy apparatus of the invention is shown schematically in perspective view in FIG. 1.

Figure 14:
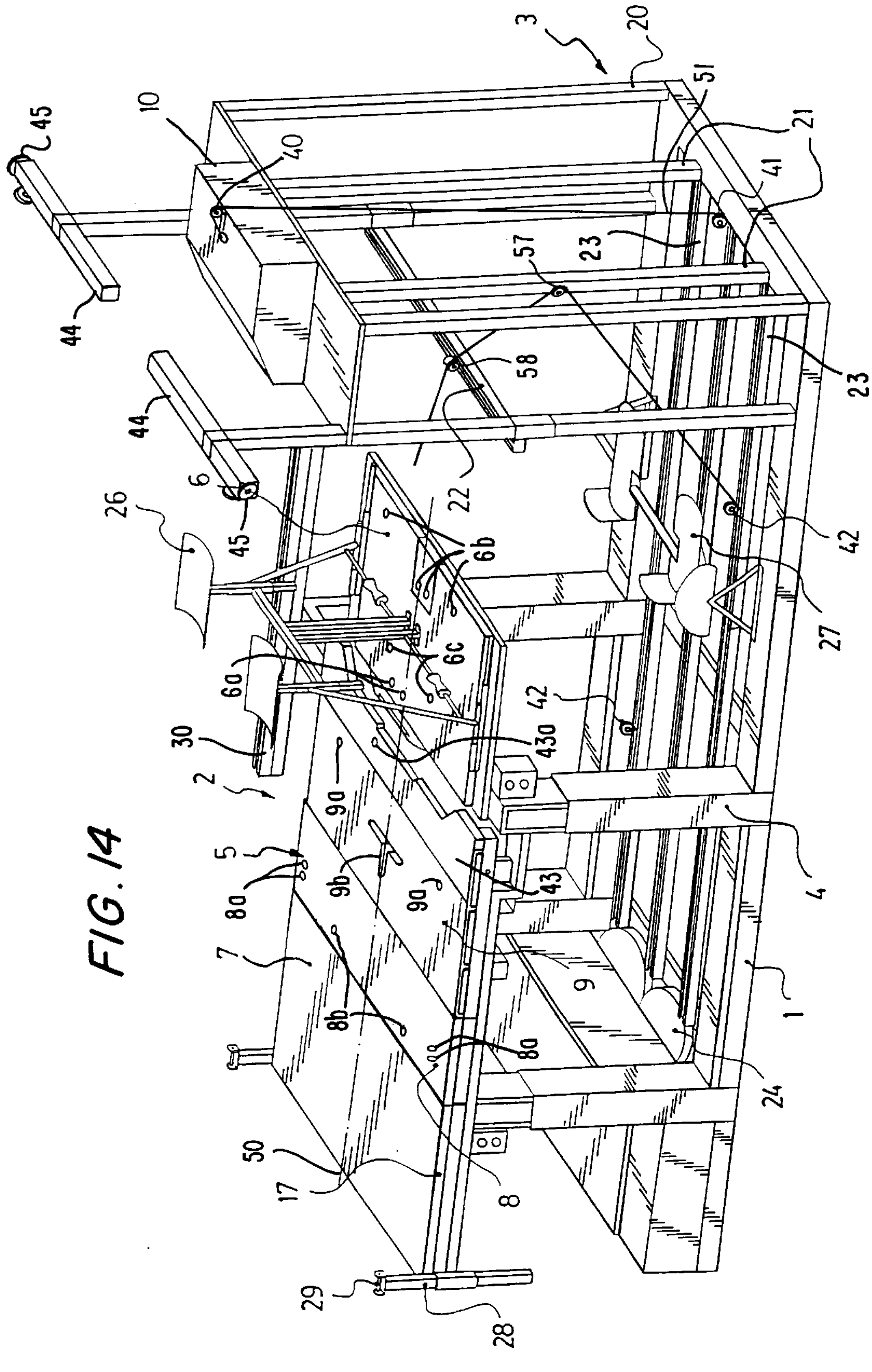
FIG. 14 is a view of the apparatus showing the cords.

As can be seen, it essentially has a base 1, on which are mounted a table 2 and a support structure 3 for a traction motor 10. The table 2 has a longitudinal axis 50 (FIG. 14).

The table 2 is mounted on the base 1 by means of four telescopic columns 4, so as to make it height-adjustable.

Figure 2:
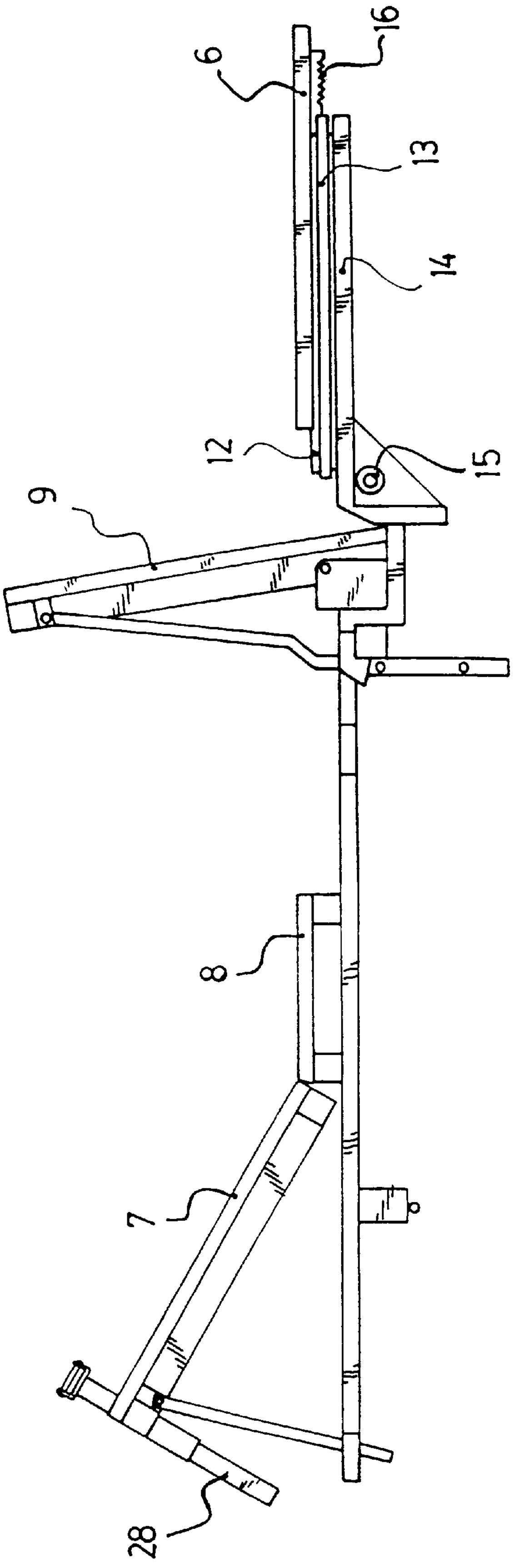
FIG. 2 is a side elevation view of the part corresponding to the table.

The table 2, which can be seen in greater detail in the elevation view of FIG. 2, is made up of a static board 5 and a moving board 6; the static table 5 is in turn made up of a first end member 7 pivoting around a first horizontal axis 53, a second fixed end member 43, a first intermediate member 8 pivoting around a second horizontal axis 54 parallel to the first and a second intermediate member 9 pivoting around a third horizontal axis 55 parallel to the first and second axes.

The moving board 6 can move on guides 12 fixed to an upper plate 13 which is in turn mounted in rotary fashion with respect to a lower base 14; this last is fitted pivotally by means of a bar 15 onto the table, so that the moving board 6 can be inclined by rotating around this bar.

Figure 5:
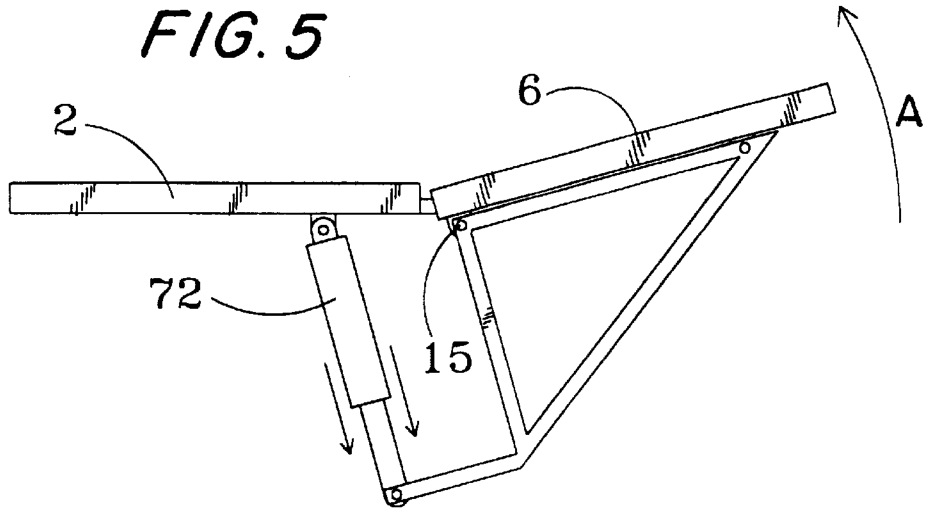
FIG. 5 is a side view of the front part of the table showing the moving board in an inclined position.
Figure 7:
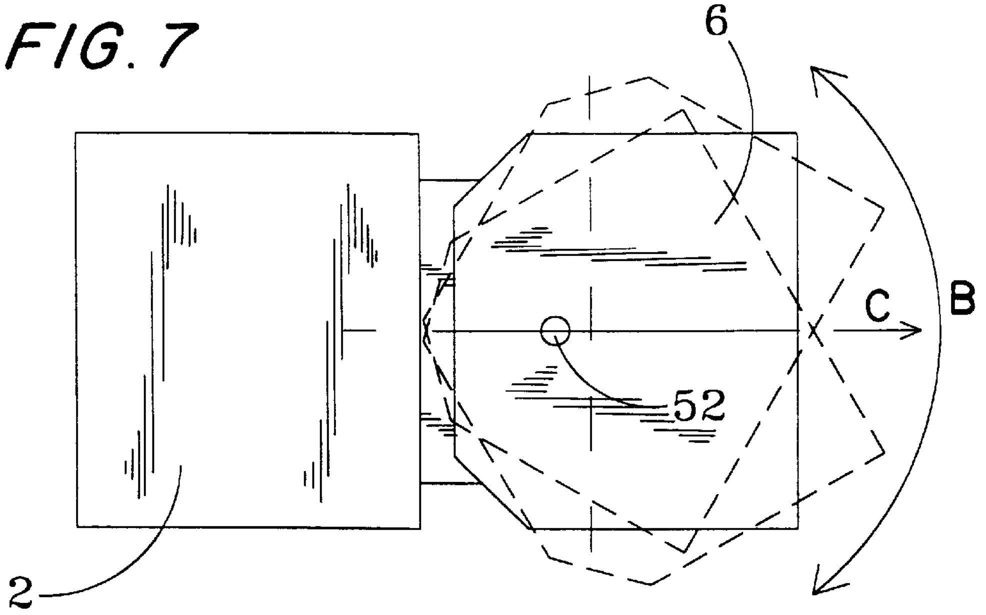
FIG. 7 is a top view of the front part of the table showing two directions of movement of the moving board.

The moving board 6 can therefore carry out three movements: inclined with respect to the table (up to approximately 50°) (as shown in FIG. 5 and represented by arrow A), rotation around an axis perpendicular to the plane of the board itself (up to approximately 30° either side from a central position of symmetry) (as shown in FIG. 7 and represented by arrow C) and withdrawing and approaching movements with respect to the static board of the table (as shown in FIG. 7 and represented by arrow B).

Some springs 16 keep the moving board 6 in its position closest to the static board 5, and to move the moving board 6 further away the force of these springs has to be overcome.

Figure 6:
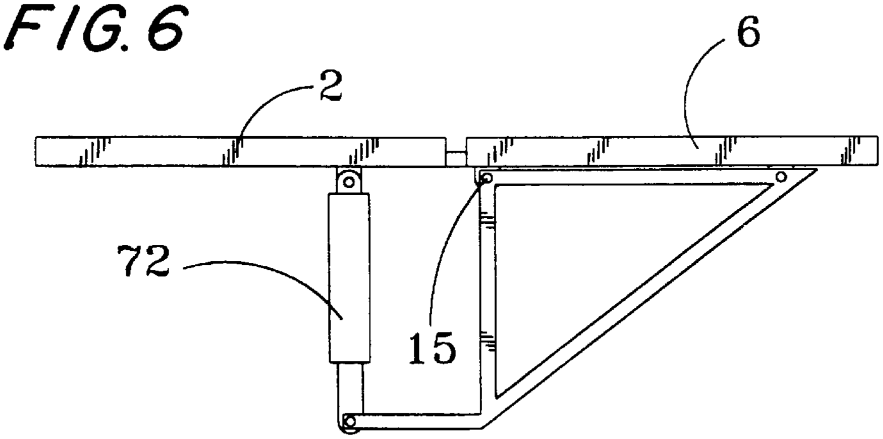
FIG. 6 is a side view of the front part of the table showing the moving board in a horizontal position.

Clearly, the three movements of the moving board could be implemented with a mechanical arrangement different from that described or shown; moreover, each one of the movements can be carried out manually or driven by an electropneumatic actuating device 72 (FIGS. 5 and 6) or the like.

Figure 8:
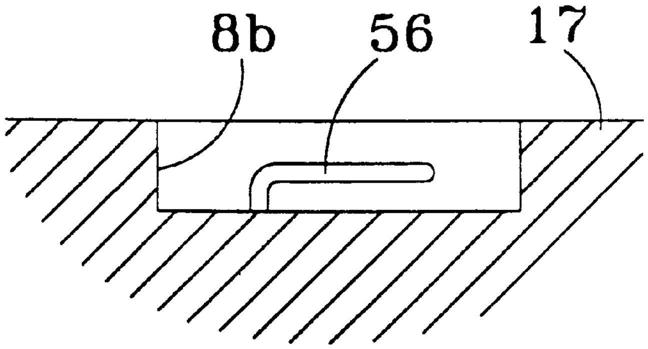
FIG. 8 is a sectional view of an anchorage point of the table.

The moving board and all the members of the fixed board are provided with covers of flexible material 17 in order to improve patient comfort; these covers have a number of openings, inside which are the anchorage points for the straps used to secure parts of the patient's body to the table (see FIG. 8).

The anchorage points are provided both on the static board 5 and the moving board 6. Specifically, on the static board, the first intermediate member 8 includes four anchorage points 8*a* arranged in pairs near both sides of same, these anchorage points 8*a* being slightly inclined and serving for securing the arm in elbow movement maneuvers. The first intermediate member 8 also includes a pair of anchorage points 8*b* fitted close to the first end member 7, which are used for securing the shoulderblade. The second intermediate member 9 includes a pair of anchorage points 9*a* fitted beside the second end member 43, which are used to secure the pelvis during hip traction. At the central part and at the same height from said anchorage points 9*a* is fitted a third T-shaped anchorage point 9*b* used to secure the thorax during lumbar traction. The second end member 43 includes a single anchorage point 43*a* situated beside the moving board 6 and centred, which is used to secure the thorax in lateralized lumbar traction. The moving board 6 includes two orifices 6*a* made close to the fixed board 5 in order to secure the pelvis. It also has four anchorage points fitted on the opposite end of said moving board 6 in order to secure the thighs in knee-movement maneuvers. The moving board 6 also has a pair of anchorage points 6*c* to secure the pelvis when the patient is seated.

The support structure 3 of the motor 10 (FIG. 1) is formed of a number of uprights 20 and vertical tubular guides 21, and also has a horizontal tubular guide 22, adjustable in height, which supports a bar with two pulleys on either end and a central attachment control for lateralization in the corresponding traction movements.

The base 1 of the apparatus is provided with three longitudinal tubular guides 23 and two return-pulleys 24.

The apparatus also includes a plurality of pulleys, which will be described in detail below but have not been shown in FIG. 1.

The apparatus of the invention is completed with a number of accessories, shown in FIG. 1 in their position of use: supports 26 for the legs, made up of a unit which can be attached to the moving board 6; tiltable attachments 27 for the feet, made up of a unit which can be attached to the base 1 of the apparatus; adjustable vertical bars 28, for example telescopic bars, fixed to the first end member 7 of the static table 5, which serve to secure the shoulder of a patient by means of straps, for which purpose they have a rod 29 on their upper end; and finally a side unit 30 of two parallel guides, which is attached to one or the other side of the table when lateral traction is required, and inside which can be fitted a pulley mounted on a slider.

Both the support 26 for the legs and the attachments 27 for the feet are fitted onto the apparatus only when required.

Figure 3:
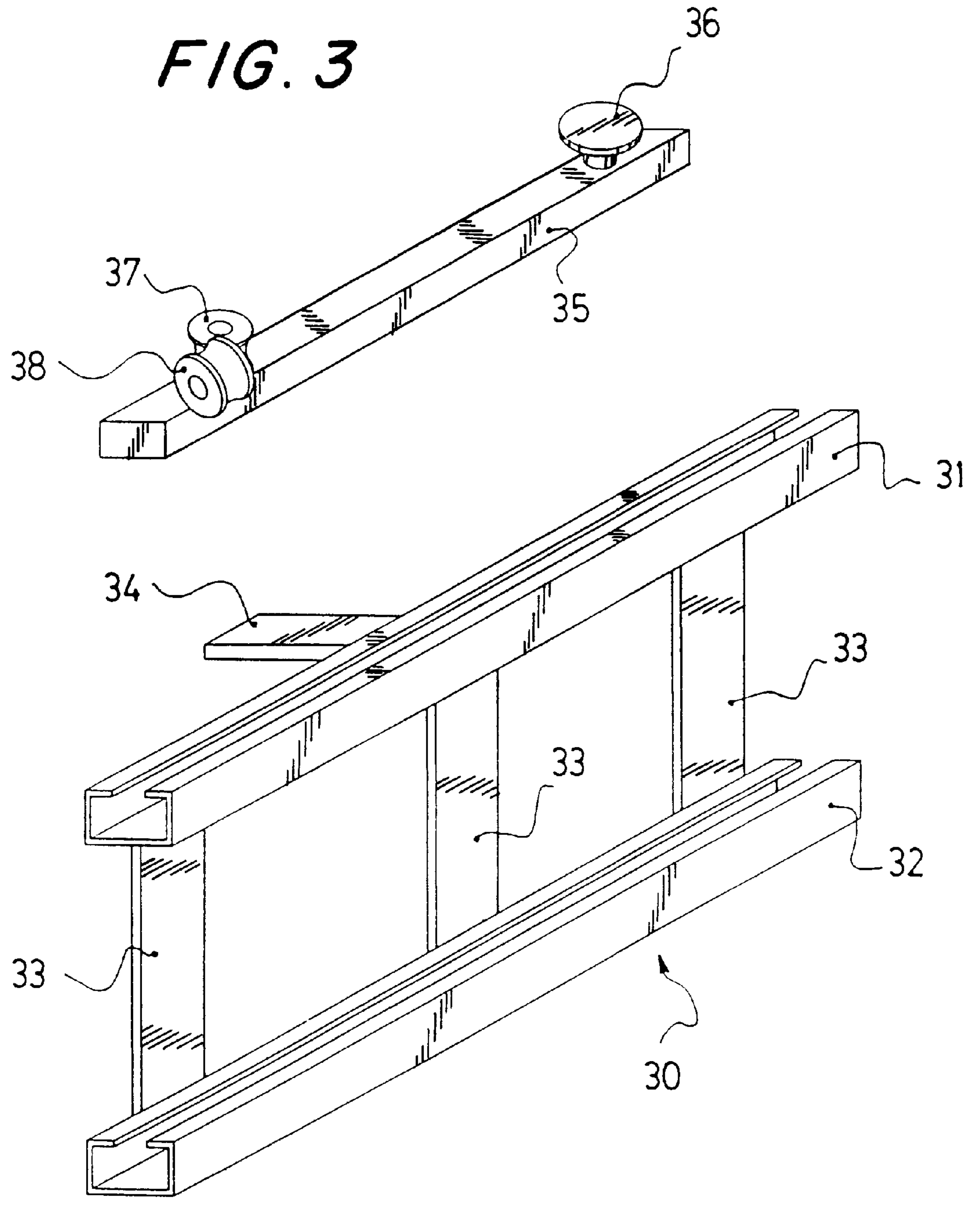
FIG. 3 is a perspective view of an accessory of the table.

The side unit 30 is shown schematically in perspective view in FIG. 3, and includes two horizontal guides 31 and 32, parallel to each other and linked by vertical bars 33, which can be associated with either side of the table by means of a coupling bar 34, which is inserted into a corresponding cavity so that the guides 31,32 are at the desired distance from the table.

Inside one of the guides 31,32 there is a cavity 131 in which can be fitted a slider 35 which is fixed in position by means of a fixing knob 36 and on which are mounted two pulleys 37,38; the pulley 37 is fixed to the slider and can rotate freely about its axis, while the pulley 38 is mounted in freely rotary fashion around the pulley 37 and around its own axis. The function of this second pulley 38 is that of guiding the cord in such a way that it always remains in the correct direction of traction.

Figure 4:
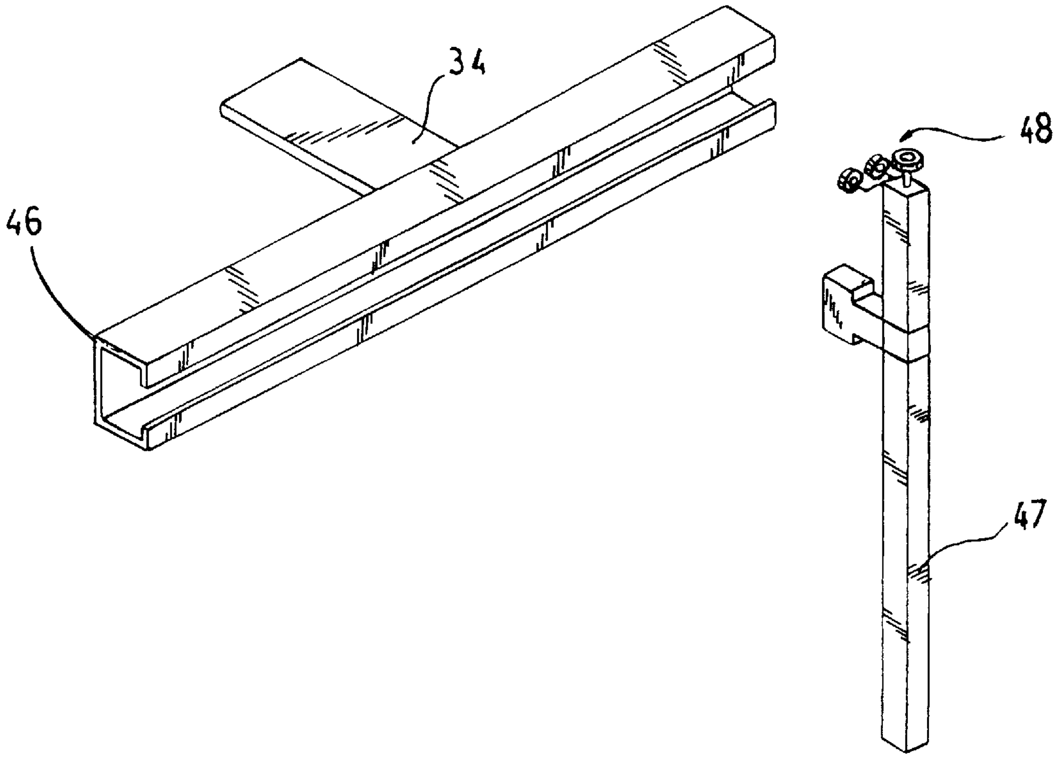
FIG. 4 is a perspective view of an accessory of the alternative table to the one shown in FIG. 3.

Alternatively, the unit 30, on the table 2 side, can be fitted with the member shown in FIG. 4, which comprises a guide 46 having a cavity 146, mounted laterally with respect to the table 2 and at an adjustable distance from it, on which guide 46 can slide a vertical telescopic bar 47 provided with a triple pulley 48 on one of its ends and slide 147. Slide 147 is structured and arranged to fit securely into cavity 146 while allowing horizontal adjustment of telescopic bar 47. This vertical bar 47 permits traction movements on the upper limbs to be carried out.

Figure 15:
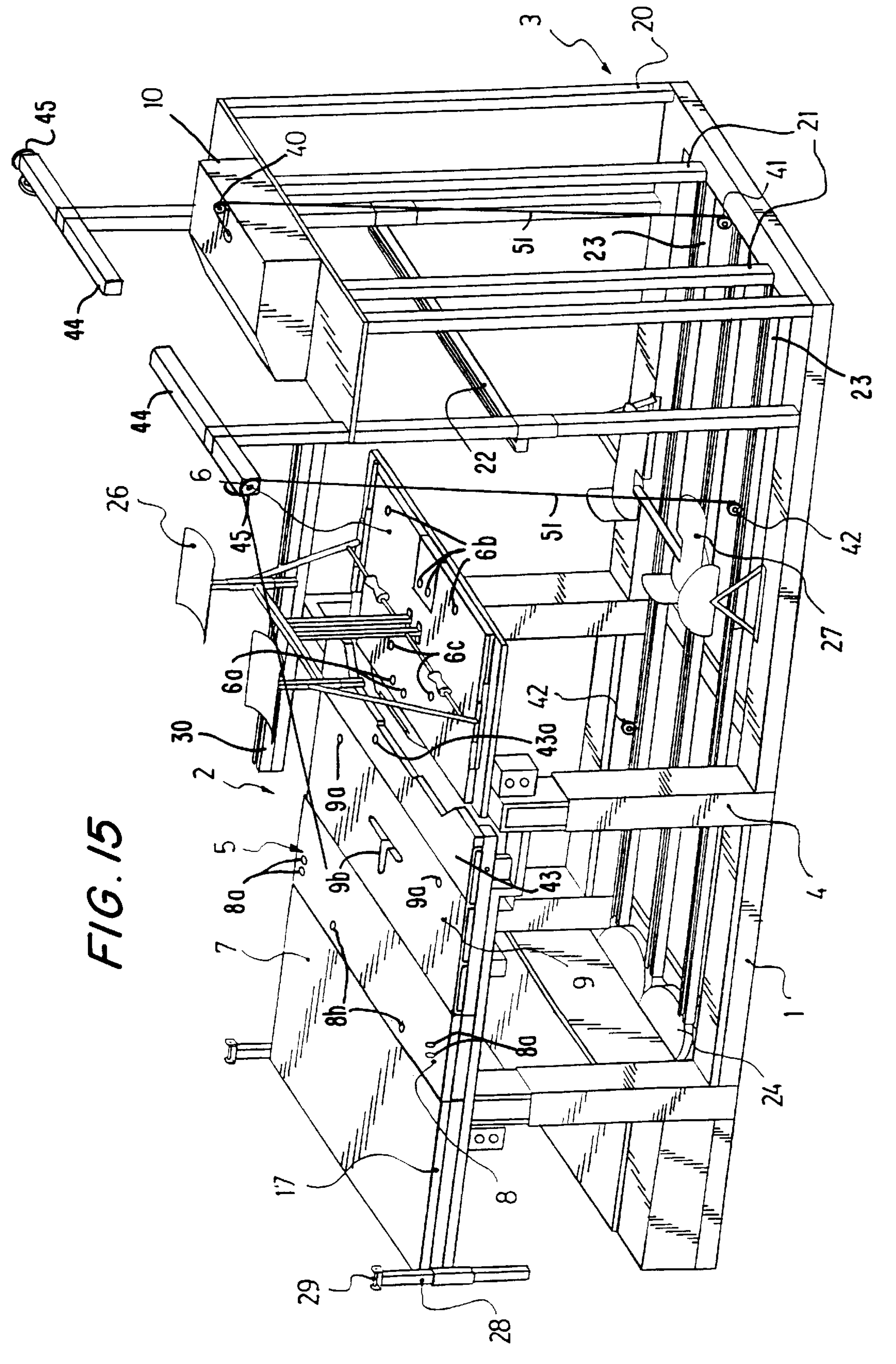
FIG. 15 is another view of the apparatus showing the cords in a different position than that shown in FIG. 14.

In order to use the apparatus described, at least one traction cord (51-FIGS. 14 and 15) is made to pass from the traction motor 10 through a number of pulleys, which vary depending on the joint to be treated, and is secured to a strap which is adjusted around part of the body of the patient in order to exercise a traction force on same. At the same time, the fixed part of the patient is in each case suitably immobilized, for example by means of another strap which fixes the corresponding part of the patient's body to the table, using the anchorage points provided for the purpose. The patient will be placed in a particular position in function of the treatment to be carried out. Descriptions are provided below by way of example of some specific treatments.

The apparatus described therefore incorporates a number of pulleys, some of them fixed and others in adjustable position, so that the traction cord or cords can be guided towards different positions of the apparatus. Some of these pulleys are mentioned below, with reference to FIG. 1.

The motor support structure 3 is provided with a driving pulley 40, through which passes a cord, the end of which is attached to the traction motor 10 outlet. On the base 1 there are two return pulleys 41, which divert the cords which then run along one of the longitudinal guides 23 (the central guide); at the opposite end of the table, each cord passes through one of the return pulleys 24 and returns along one of the longitudinal guides 23.

On these guides are provided pulleys 42 of adjustable position throughout the length of the guide, from which pulleys the cords can be directed towards different points of the apparatus.

The vertical tubular guides 21 and the horizontal tubular guide 22 are also provided with adjustable-position pulleys (not shown).

Figure 9:
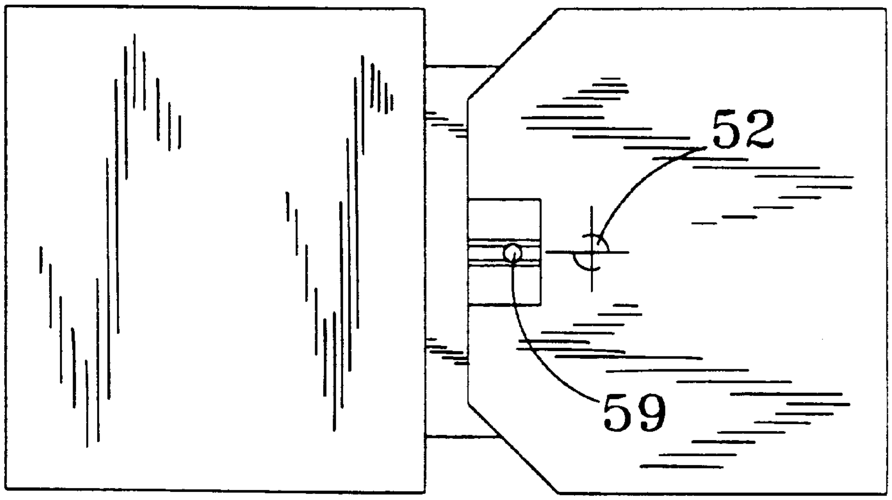
FIG. 9 is a top view of the front part of the table.

The system of pulleys also includes an adjustable-position pulley 59 inside a guide fixed to the lower board of the moving board 6 (FIG. 9), being therefore situated under the table, and also a pulley mounted on a bracket for cervical vertebra traction (not shown), which can where necessary be attached to the motor support structure 2.

On the motor support structure 2 are provided a pair of horizontal telescopic bars 44 one of whose ends has a triple pulley 45. These horizontal bars 44 allow cervical vertebra traction forces to be oriented towards any degree.

Figure 10:
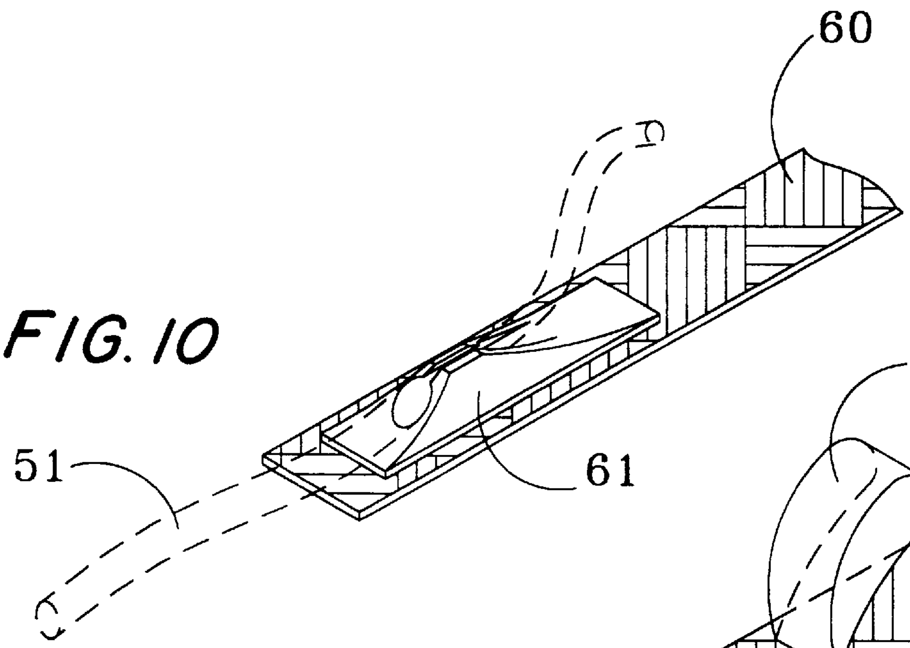
FIG. 10 show one type of strap used in the invention.
Figure 11:
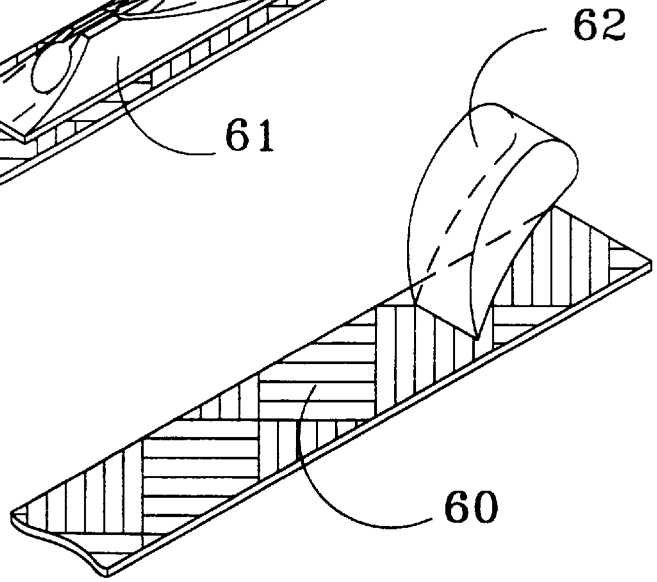
FIG. 11 shows a second type of strap used in the invention.
Figure 12:
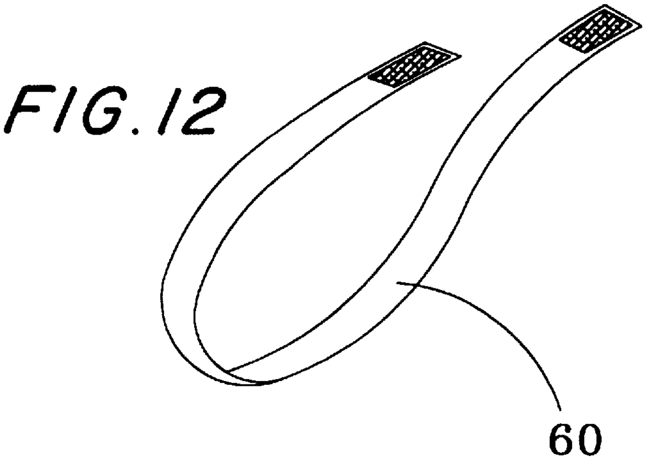
FIG. 12 shows a third type of strap used in the invention.

In order to immobilize part of the body of the patient during a treatment session, and also to apply traction to the joint to be treated, a number of straps have been provided (designated 60 as shown in FIGS. 10–12): depending on the use of each strap (to secure the patient's body to the table or to secure a limb in order to apply traction to it) and on the part of the body for which the strap is used, several types of straps can be provided, only some of which will be described.

Some straps have a band destined to run around a part of the patient's body, to which band are attached two tubular fitments provided with means for tightening 61 onto two cords inserted into them (FIG. 10); others have a band destined to run around a part of the patient's body and have attached to them a strip (62 FIG. 11) whose free end forms an eye for coupling with some anchoring rods 56 (FIG. 8) provided at suitable positions on the surfaces of the boards.

The tightening of some of the straps can be carried out with Velcro-type closures (FIG. 12); the straps which are destined for attachment to the part of the body subjected to traction (instead of to the fixed part, secured to the table) have means for tying one of the traction cords to same.

Specified below are some of the various treatments which can be carried out with the physiotherapy apparatus described, which include traction movements on the large joints over any arc within the articular limits according to the therapeutic needs of the patient.

a) Cervical column: axial traction, or traction with right or left lateralization component. Patient position: dorsal decubitus with or without cervical flexion.

b) Lumbar column: axial traction, traction with right or left lateralization component, anti-lordosis manoeuvre. Patient position: dorsal decubitus with suitable degree of lumber delordosis.

c) Shoulder: axial traction in any articular arc of suitable abduction, caudal-transfer traction in any suitable articular arc of abduction, side transfer traction in any suitable articular arc of flexion according to pathology. Patient position: dorsal decubitus.

d) Elbow: dorsal transfer movements in any suitable arc. Patient position: dorsal decubitus.

e) Hip: axial traction in any articular abduction arc, caudal- or lateral-transfer traction in any articular flexion arc, axial abduction within the articular limits. Patient position: dorsal decubitus.

f) Knee: axial traction in any articular arc, with varus or valgus component, dorsal-transfer traction in any articular flexion arc, ventral-transfer traction in any articular extension arc, angular mobilizations in any articular flexion and extension arc. All the movements can also be carried out with a rotation component. Patient position: seated or decubitus, according to the manoeuvre.

g) Ankle: axial traction, dorsal-transfer traction, ventral-transfer traction, all in any articular arc. Patient position: seated.

h) Wrist: axial traction in any flexion or extension position, and with any cubital and/or radial deviation component desired.

A detailed description of some of these treatments is provided below; as will be seen, in each case the patient must be positioned and immobilized suitably, and this will vary considerably from one treatment to another, so that the versatility of the apparatus described is of considerable importance.

For treatment of the shoulder, for example, the patient will lie flat in decubitus, with the head resting in the first end member 7 of the static board 5 of the table (see FIG. 1), and part of the shoulder is immobilized using a strap which is secured to the adjustable vertical bar 28 situated on the opposite side of the table from the shoulder to be treated. A traction cord is then made to pass from the pulley 42, situated at an intermediate point on its corresponding longitudinal guide 23, through the pulleys 37,38 mounted at a suitable position on the unit of parallel guides (FIG. 3), and is attached to a strap which secures the patient's arm. A suitable traction cycle is then carried out. It should be noted that the rotary pulley 38 ensures optimum direction of traction at all times.

In the case of lumbar treatments, the patient is also positioned with head resting on the first end member 7 of the static board 5, and is immobilized as follows: the chest is secured by means of strap to the static board 5, and the abdomen is secured by means of another strap to the moving board 6; the moving board 6 is then oriented in the desired way, thanks to its two possible rotations, a traction cord is attached to this moving board and the desired traction cycle is then carried out.

In the case of ankle axial and transfer treatments, the patient sits on the moving board 6, while the end member 9 of the static board 5 is raised and used in this case as backrest.

The patient's foot is immobilized in the attachments 27 by means of a suitable strap, and the desired traction cycle is carried out through another strap attached to the leg above the ankle. Depending on whether the traction is dorsal or ventral, the pulley 42 which guides the traction cord will be situated at a particular position along the longitudinal guide 23.

Figure 13:
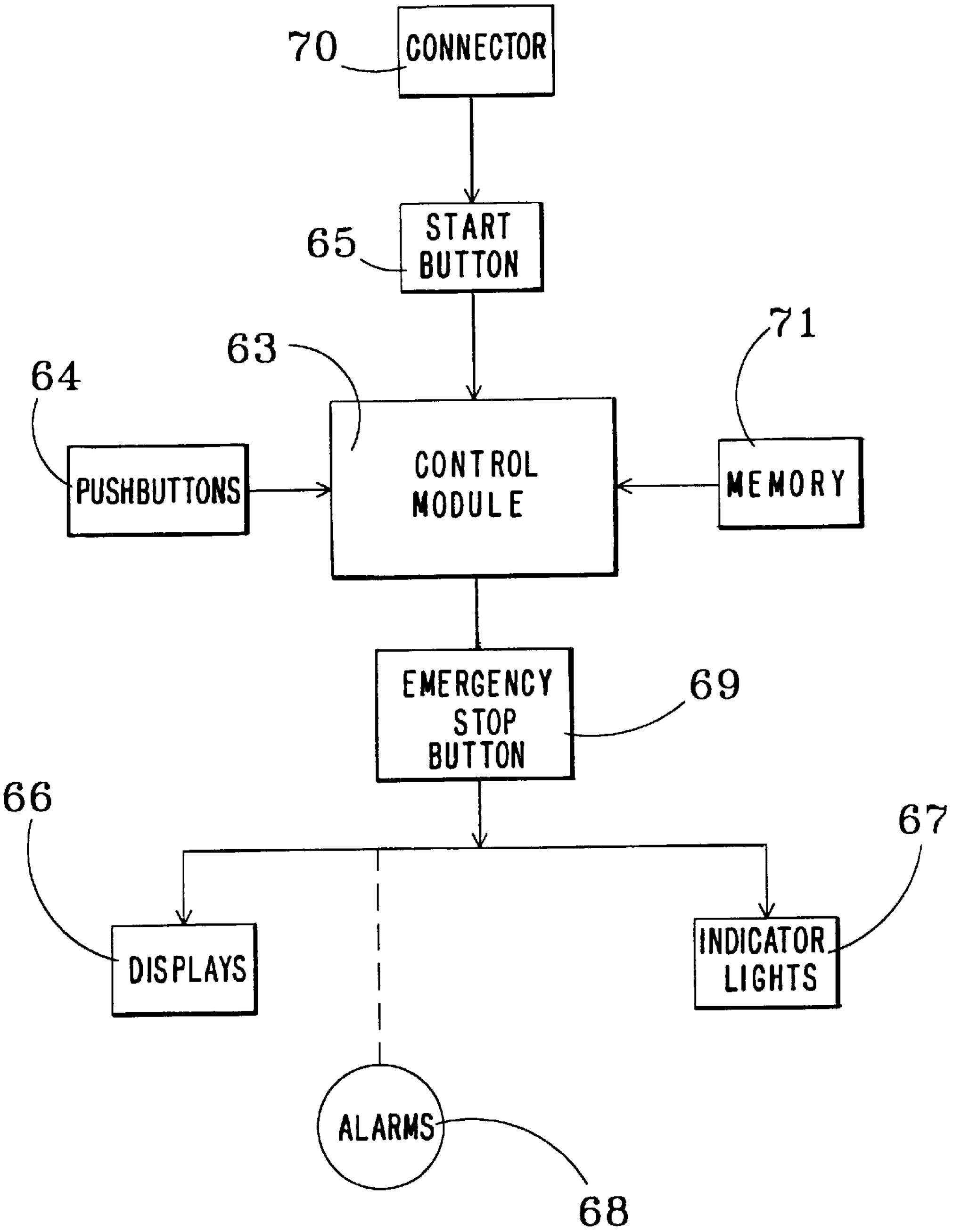
FIG. 13 is a diagram of the function of the motor.

The traction motor 10 is adjustable, in order to provide the traction force best suited to each case; in order to permit reliable and safe operation the apparatus is provided with a motor 10 control module (63-FIG. 13) which includes a plurality of pushbuttons 64 for adjusting/setting treatment parameters, a start button 65, displays 66 for parameters selected, and indicator lights 67 showing the treatment selected and the treatment phases.

The control module permits programming of: treatment type (cervical, lumbar vertebrae, etc.); treatment time, following which the motor stops and the cord loses tension; traction and relaxation times and forces; and traction and relaxation speeds.

Once the parameters have been programmed, the start button causes the treatment to start and the apparatus will switch automatically between traction and relaxation in accordance with the programming carried out.

For greater safety, the control module further includes a set of alarms 68, an emergency stop pushbutton 69 and a connector 70 for a remote-control cable, so that both physiotherapist and patient can stop the treatment if they deem such to be appropriate. There are also detectors which halt operation of the apparatus is there is any overload, for example, if the force exceeds the programmed value by 10% or if stretching breakdown occurs.

The control module includes a non-volatile memory 71 for storing the standard values for each treatment; once the treatment has started, one or more parameters can be altered from the control module in order better to adapt the treatment initially set to the needs of each patient.

Using the control module it is possible to carry out traction movements on any joint or group of joints in a dosified and controlled way within the seven motor programs.

In order to facilitate transportation thereof, the physiotherapy apparatus of the invention can be separated into at least three parts or units.

I claim:

1. A physiotherapy apparatus for treatment of articular rigidity, comprising a base;

a support structure coupled to said base;

a table on which a patient lies, said table being connected to said support structure and including a static board and a planar moving board movable to variable distances in the longitudinal direction from said static board, said moving board having a first position in which said moving board is situated in a horizontal plane and being pivotally mounted to said support structure such that said moving board is movable between a flat, horizontal position in said horizontal plane and an inclined position in which said moving board is at an angle relative to said horizontal plane, said moving board being rotatable about an axis perpendicular to said horizontal plane, said moving board comprising a horizontal bar connected to said support structure, said moving board being pivotable relative to said support structure about said horizontal bar, a lower base attached to said horizontal bar, an upper plate rotatable relative to said lower base about the axis perpendicular to said horizontal plane, and a pair of guides fixed to said upper plate for enabling said moving board to be moved toward and away from said static board in said longitudinal direction of said table;

traction means for applying a traction force between parts of the patient's body, said traction means including at least one traction cord and a system of pulleys associated with said at least one traction cord whereby said at least traction cord runs around at least one of said pulleys; and elastic means for maintaining said moving board in a symmetrical position with respect to a longitudinal axis of said table and biasing said moving board toward said static board.

2. The apparatus of claim 1, wherein said static board comprises a first end member pivotally mounted to said support structure about a first horizontal axis, a second end member fixed to said support structure, a first intermediate member pivotally mounted to said support structure about a second horizontal axis parallel to said first horizontal axis, and a second intermediate member pivotally mounted to said support structure about a third horizontal axis parallel to said first and second horizontal axes.

3. The apparatus of claim 1, wherein said support structure comprises telescoping uprights having an adjustable height, said static board and said moving board being connected to said uprights.

4. The apparatus of claim 1, wherein both said static board and said moving board further comprises anchorage points for releasably attaching straps adapted to secure the patient to said static board and said moving board.

5. The apparatus of claim 4, further comprising an anchoring rod arranged at each of said anchoring points.

6. The apparatus of claim 1, further comprising an adjustable traction motor for providing tension to said at least one traction cord, said support structure comprising supporting uprights extending vertically from said base and being connected to said table at a height above said base, and a second support structure on which said traction motor is mounted.

7. The apparatus of claim 6, wherein said at least one traction cord comprises two traction cords attached to said traction motor, the apparatus further comprising longitudinal guides fixed to said base, said system of pulleys comprising at least one driving pulley arranged on said second support structure alongside said traction motor, a double return-pulley arranged at a first end of said base adjacent said second support structure, a pair of horizontal pulleys arranged at a second end of said base opposite said first end of said base, and a pair of displaceable pulleys along said longitudinal guides, each of said displaceable pulleys guiding a respective one of said two traction cords.

8. The apparatus of claim 7, further comprising vertical guides mounted to said second support structure, a horizontal guide mounted to said second support structure, said horizontal guide being vertically movable, said system of pulleys further comprising a pair of vertically movable pulleys movable along said vertical guides, and a pair of horizontally movable pulleys movable along said horizontal guide.

9. The apparatus of claim 7, wherein said system of pulleys further comprises at least one pulley mounted on a support for cervical vertebrae traction and wherein said at least one pulley is releasably fixed to said second support structure.

10. The apparatus of claim 7, further comprising a set of two parallel guides mounted laterally with respect to said table and at an adjustable distance from said table, a slider movable in said two parallel guides, and said system of pulleys further comprising at least one lateral guide pulley mounted on said slider.

11. The apparatus of claim 7, further comprising an additional guide attached to said moving board, and said system of pulleys further comprising a central pulley movable along said additional guide.

12. The apparatus of claim 7, wherein said system of pulleys further comprises a cord-direction guiding pulley.

13. The apparatus of claim 7, wherein said second support structure includes a pair of telescoping, horizontal bars, said system of pulleys further comprising pulleys arranged at an end of each of said bars for cooperating with said at least one traction cord.

14. The apparatus of claim 1, further comprising leg supports adjustably and releasably mounted on said static board, and foot supports adjustably and releasably mounted on said base.

15. The apparatus of claim 1, wherein said static board comprises a first end member pivotally mounted to said support structure about a first horizontal axis and a second end member fixed to said support structure, the apparatus further comprising vertical, telescoping bars connected to lateral sides of one of said first and second end members, each of said bars including a rod at an upper end adapted to secure a strap.

16. The apparatus of claim 1, further comprising straps for securing the patient to said table or for coupling said table to said at least one traction cord.

17. The apparatus of claim 16, wherein at least one of said straps includes a tubular fitment for receiving said at least one traction cord and enabling tightening of said at least one traction cord.

18. The apparatus of claim 16, wherein at least one of said straps includes a strip having a free end forming an eye, said table including an anchoring rod for receiving said eye.

19. The apparatus of claim 1, further comprising an adjustable traction motor for providing tension to said at least one traction cord, and a control module for controlling said traction motor.

20. The apparatus of claim 19, wherein said control module includes pushbuttons for setting parameters for the treatment, a pushbutton for starting said traction motor, display for displaying the parameters for the treatment, indicator lights for indicating the treatment and the parameters for the treatment, alarms, an emergency stop button and a connector for a remote-control cable.

21. The apparatus of claim 20, wherein said control module further includes a non-volatile memory for storing standard values for the treatment.

22. The apparatus of claim 1, further comprising a guide mounted outward of said table and at a distance from a side of said table, a telescoping, vertical bar arranged on said guide, and said system of pulleys comprising pulleys arranged on said bar for cooperating with said at least one traction cord.

* * * * *

UNITED STATES PATENT AND TRADEMARK OFFICE

CERTIFICATE OF CORRECTION

PATENT NO. : 6,102,882
DATED : August 15, 2000
INVENTOR(S) : Cobo

It is certified that error appears in the above-identified patent and that said Letters Patent is hereby corrected as shown below:

Please change filing date from "April 15, 1996" to --April 10, 1997--.

Signed and Sealed this

Seventeenth Day of July, 2001

Nicholas P. Godici

Attest:

NICHOLAS P. GODICI

*Attesting Officer* *Acting Director of the United States Patent and Trademark Office*